United States Patent [19]
Satter et al.

[11] 4,273,187
[45] Jun. 16, 1981

[54] PETROLEUM RECOVERY CHEMICAL RETENTION PREDICTION TECHNIQUE

[75] Inventors: Abdus Satter; Richard H. Widmyer; Yick M. Shum, all of Houston; Curtis E. Howard, Porter, all of Tex.

[73] Assignee: Texaco Inc., White Plains, N.Y.

[21] Appl. No.: 61,963

[22] Filed: Jul. 30, 1979

[51] Int. Cl.$^3$ ............................ E21B 47/00; E21B 49/00
[52] U.S. Cl. .............................................. 166/250; 166/252
[58] Field of Search ................... 166/250, 252; 73/151, 73/155; 23/230 EP

[56] References Cited
U.S. PATENT DOCUMENTS

| | | | |
|---|---|---|---|
| 3,427,652 | 2/1969 | Seay | 73/151 X |
| 3,508,876 | 4/1970 | Polly | 166/252 X |
| 4,058,366 | 11/1977 | Cabbiness | 166/250 X |
| 4,090,308 | 5/1978 | Deans et al. | 166/250 X |
| 4,099,565 | 7/1978 | Sheely et al. | 166/252 |
| 4,168,746 | 9/1979 | Sheely | 166/252 |

OTHER PUBLICATIONS
Dalton et al., "Single-Well Tracer Method to Measure Residual Oil Saturation," SPE Paper No. 3792, 1972.

*Primary Examiner*—Stephen J. Novosad
*Assistant Examiner*—George A. Suchfield
*Attorney, Agent, or Firm*—Carl G. Ries; Robert A. Kulason; Jack H. Park

[57] ABSTRACT

The amount of a petroleum recovery chemical retained within a subterranean reservoir is predicted by first gathering data from at least one injection-soak-production cycle in a single well wherein the produced fluids are monitored for both the chemical concentration in the produced fluid as well as the concentration of a nonabsorbing tracer and, second, utilizing this data in a chemical flood mathematical model to simulate at least one repetition of the injection-soak-production cycle. The simulated cycles are repeated until the simulated produced fluid concentration of the chemical is virtually the same as the actual produced fluid concentration of the nonabsorbed tracer. The amount of the chemical retained per unit of reservoir volume is then determined by conventional techniques.

8 Claims, 9 Drawing Figures

SURFACTANT AND TRACER CONCENTRATION PROFILES IN A CYCLIC TEST

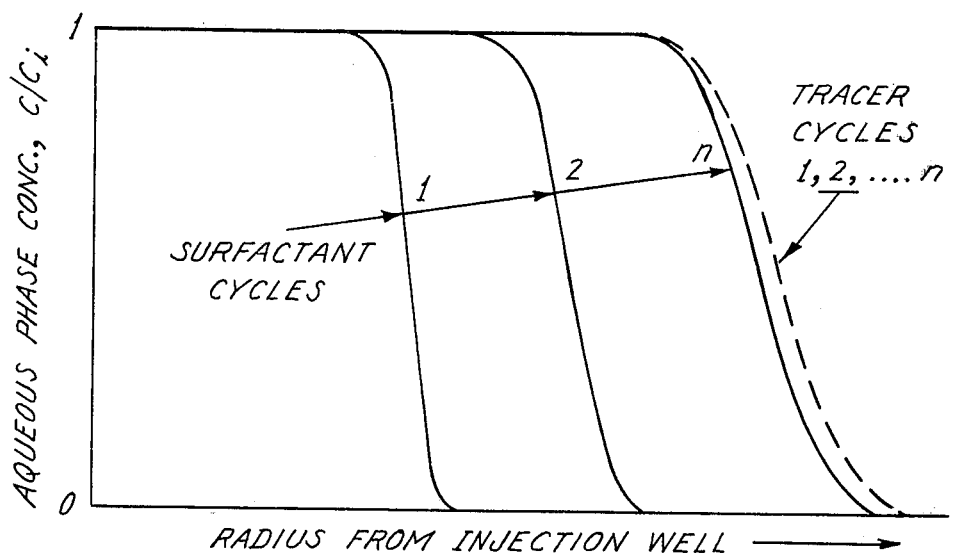
Fig. 1 SURFACTANT AND TRACER CONCENTRATION PROFILES IN A CYCLIC TEST
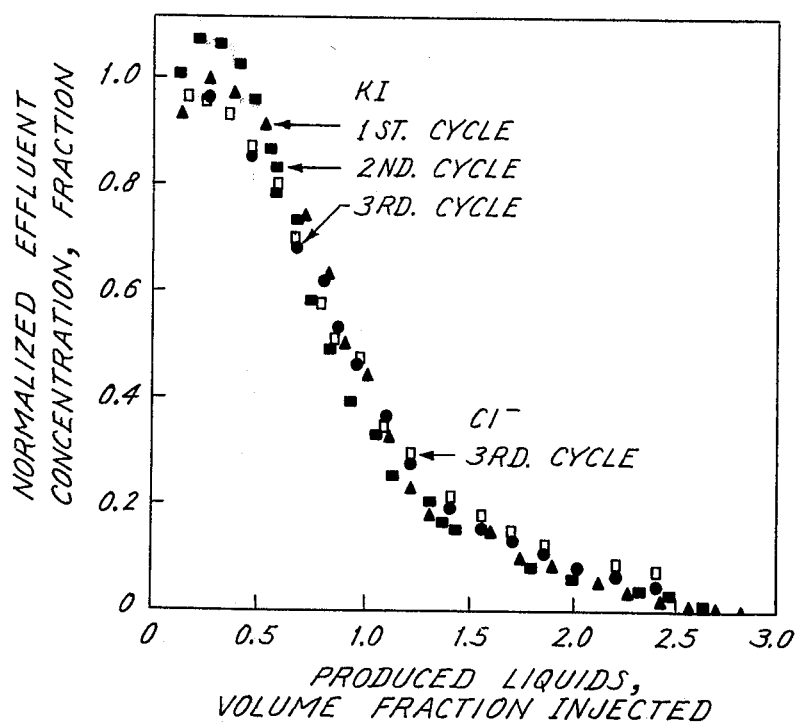
Fig. 2 NORMALIZED PRODUCED KI AND $Cl^-$ CONCENTRATIONS

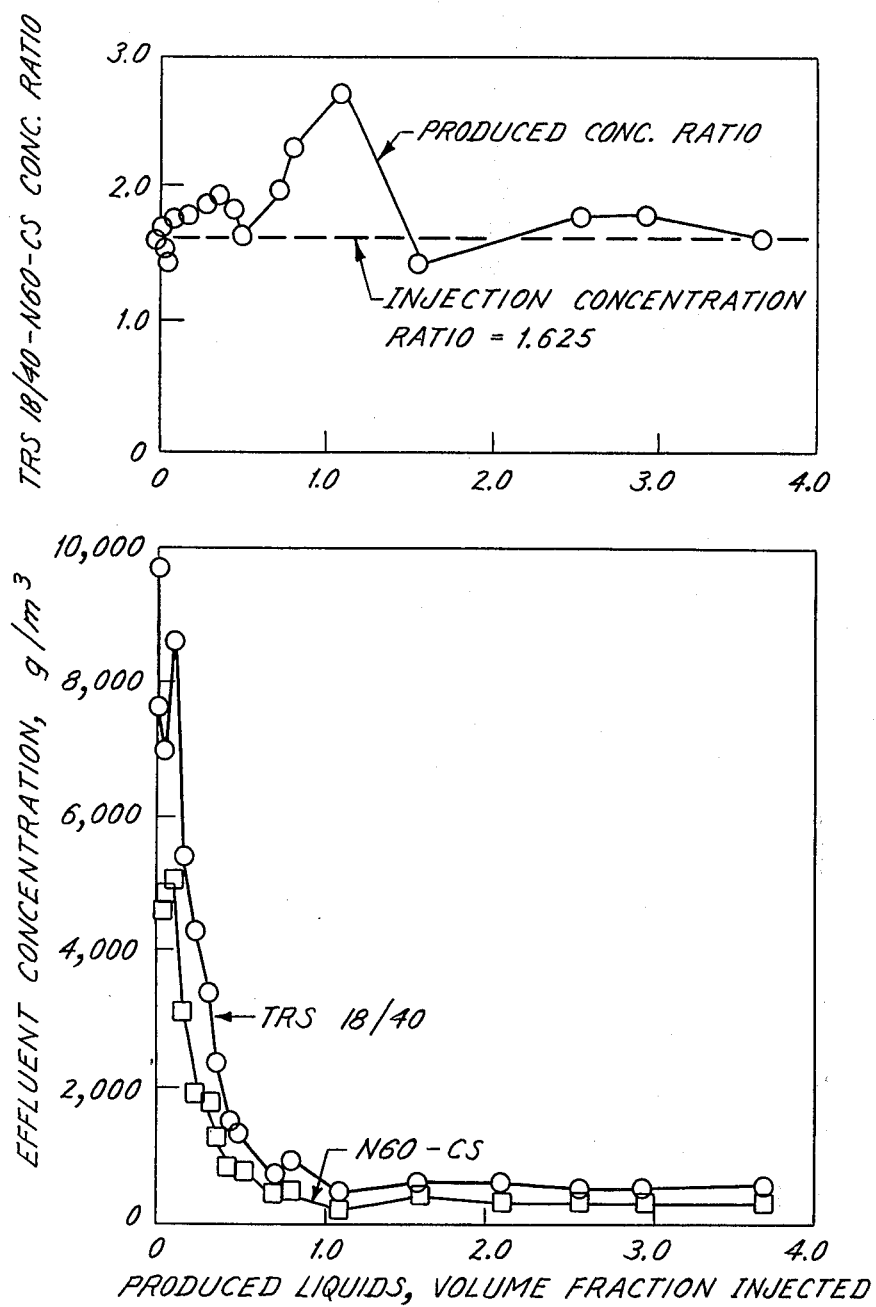
Fig. 3 FIRST CYCLE PRODUCED SURFACTANT CONCENTRATIONS

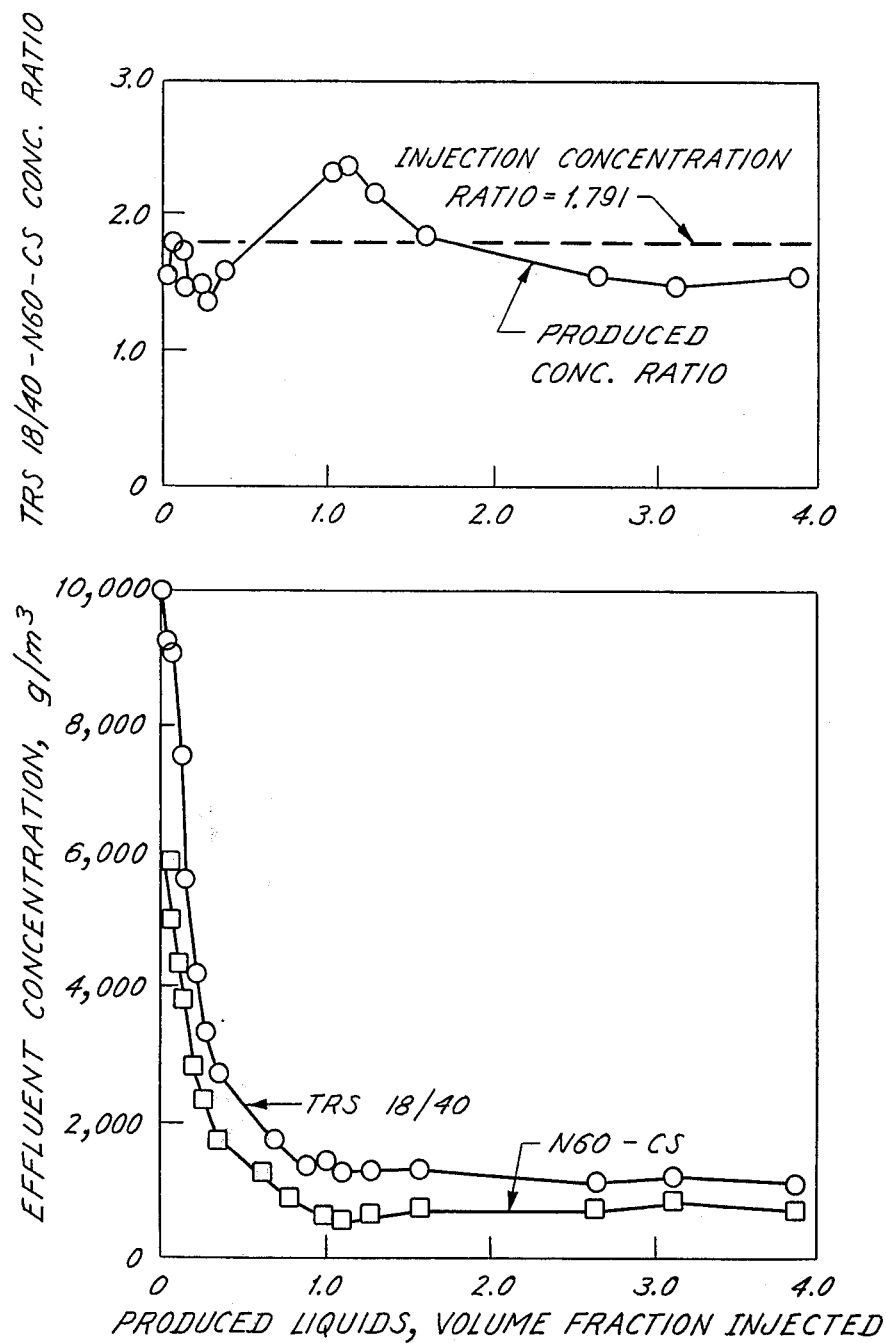
Fig. 4 SECOND CYCLE PRODUCED SURFACTANT CONCENTRATIONS

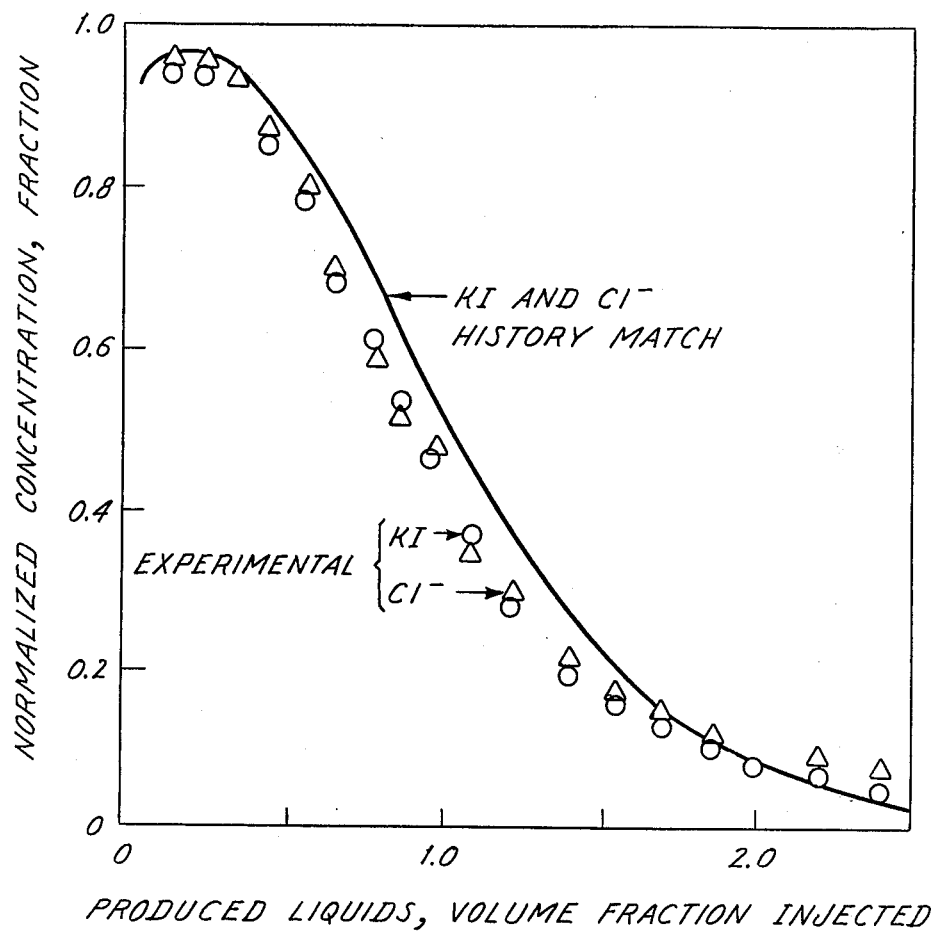
Fig. 5  THIRD CYCLE KI AND CI⁻ PRODUCTION RESPONSES

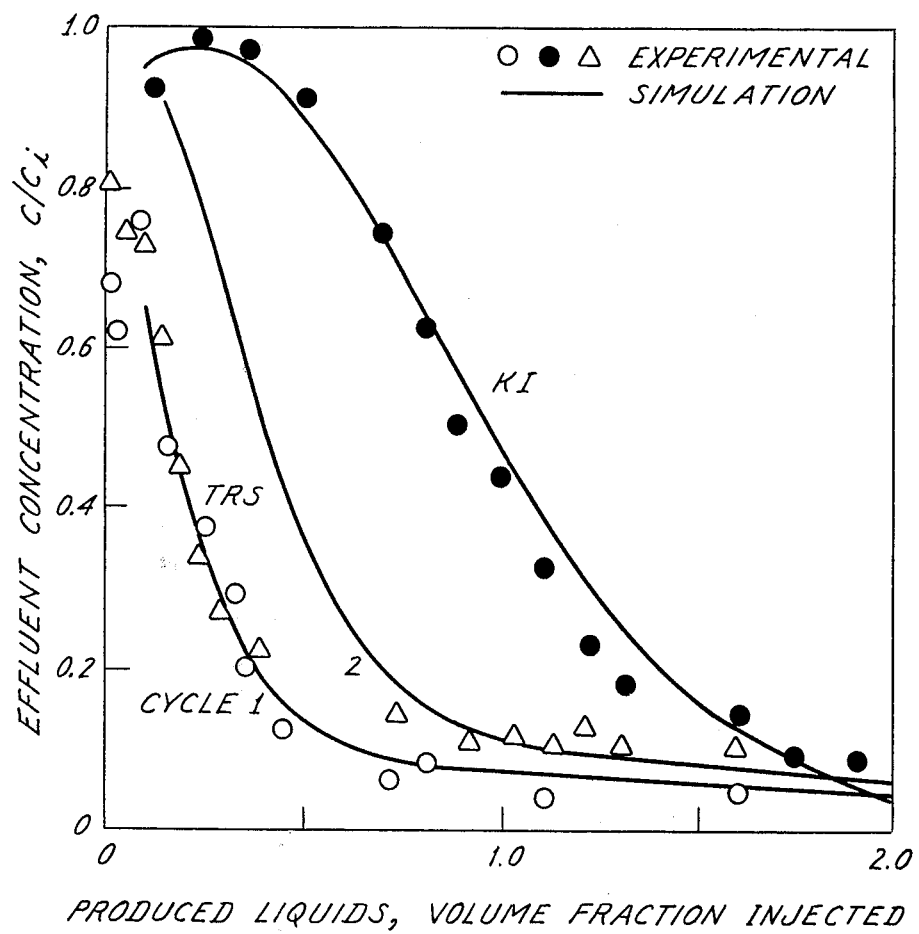
Fig. 6  TRS AND KI RESPONSES

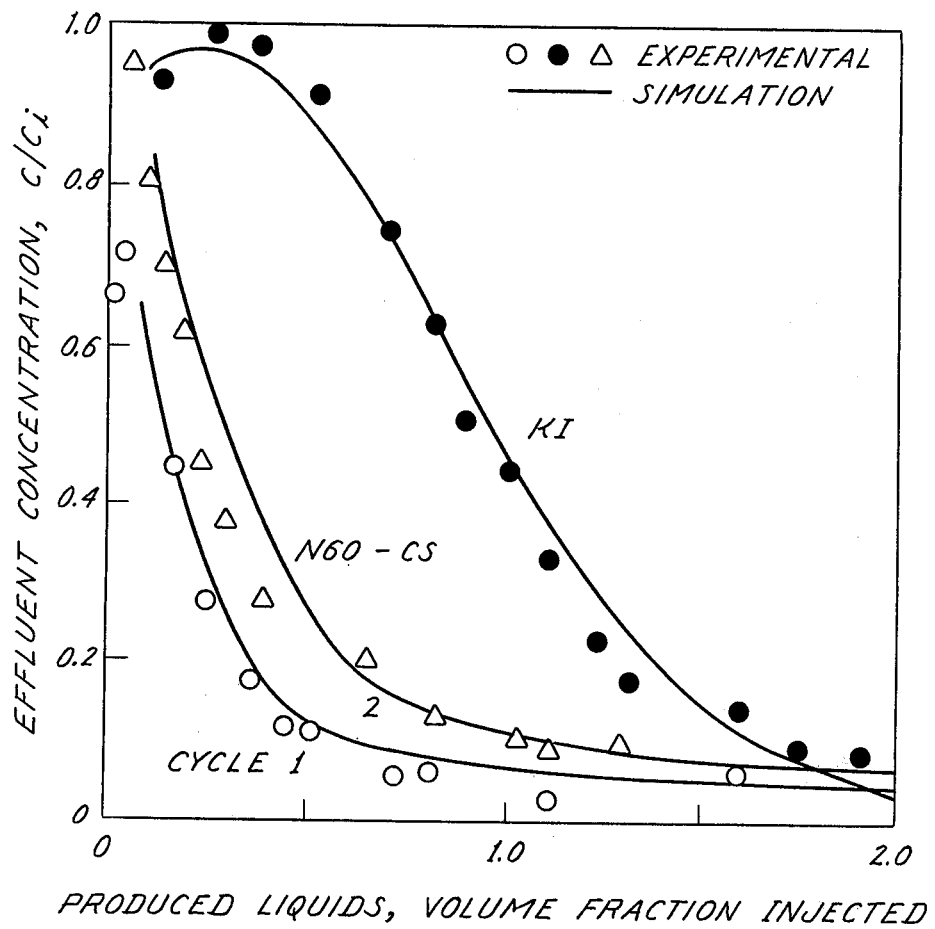
Fig. 7 N60-CS AND KI RESPONSES

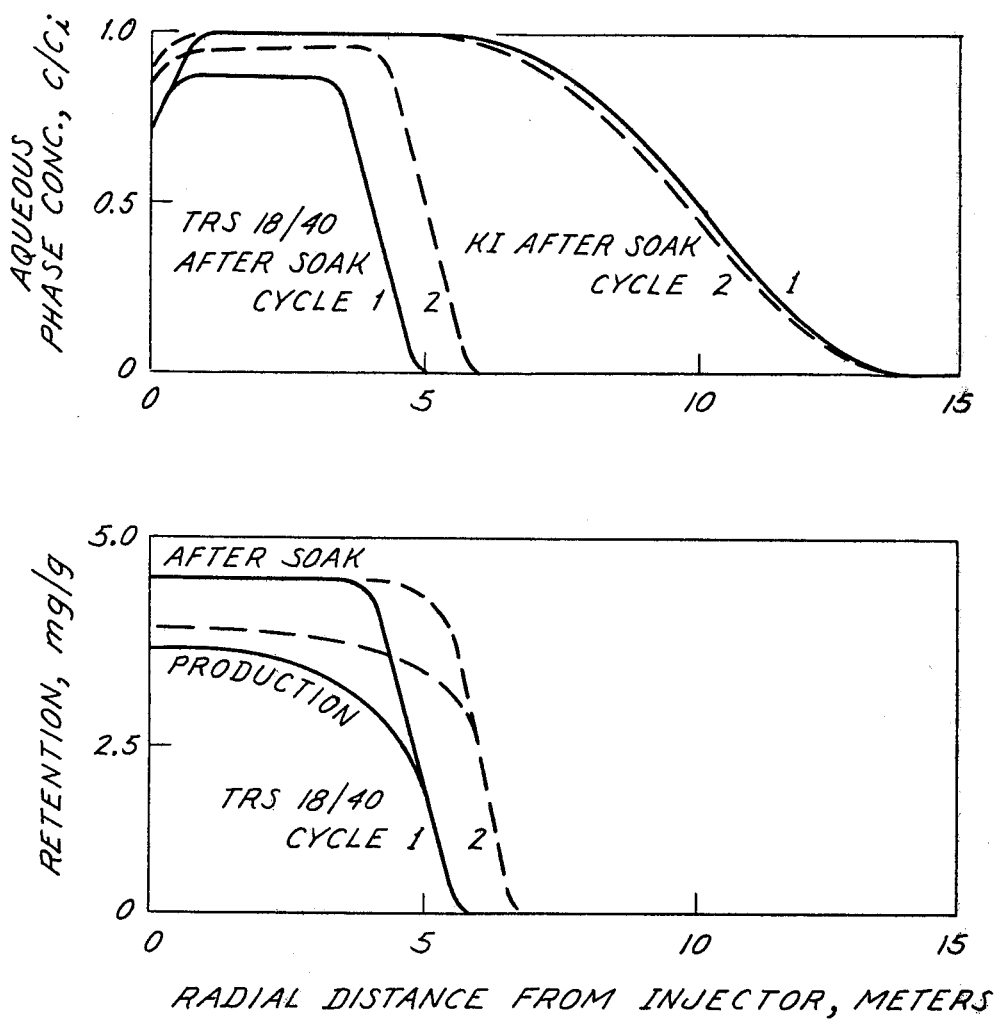
Fig. 8  TRS 18/40 AND KI CONCENTRATION DISTRIBUTIONS

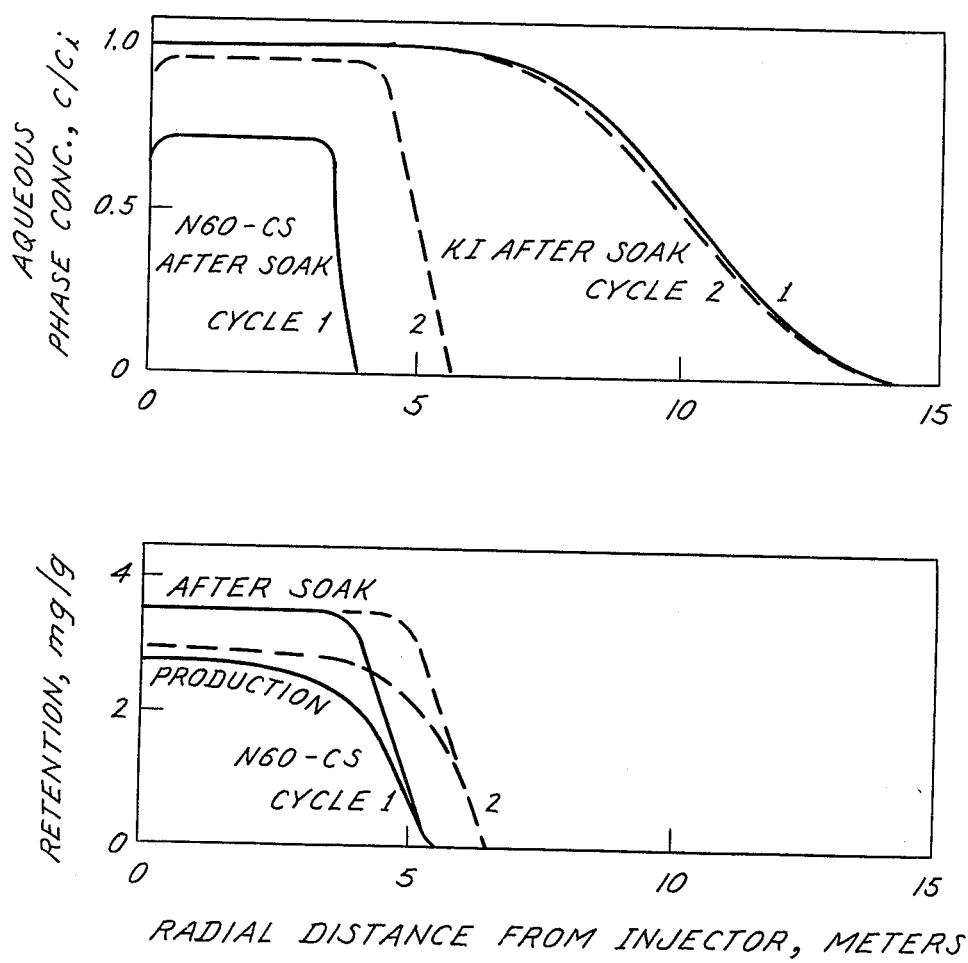
Fig. 9  N60-CS AND KI CONCENTRATION DISTRIBUTIONS

PETROLEUM RECOVERY CHEMICAL RETENTION PREDICTION TECHNIQUE

BACKGROUND OF THE INVENTION

1. Field of the Invention

This invention concerns an oil recovery process and more specifically is concerned with a method for predicting the amount of chemicals retained within a subterranean reservoir during the course of an oil recovery process.

2. Description of the Prior Art

The crude oil which has accumulated in subterranean reservoirs is recovered or produced through one or more wells drilled into the reservoir. Initial production of the crude oil is accomplished by a primary recovery technique wherein only the natural forces present in the reservoir, such as gas drive and natural water drive, are utilized to produce the oil. However, upon depletion of these natural forces and the termination of primary recovery, a large portion of the crude oil remains trapped within the reservoir. Also, many reservoirs lack sufficient natural forces to be produced by primary methods from the very beginning. Recognition of these facts has led to the development and use of many enhanced oil recovery techniques. Most of these techniques involve injection of at least one fluid into the reservoir to produce an additional amount of the crude oil therefrom.

Water flooding involves injection of water into the subterranean oil reservoir for the purpose of displacing the crude oil from the pore spaces of the reservoir rock towards the producing wells. It is the most economical and widely used of the enhanced oil recovery methods. Nevertheless, water does not displace oil with high efficiency because of the high interfacial tension between water and oil and because of the resulting immiscible displacement of oil by water.

Because of the inherent low efficiency of the basic water flooding method, the petroleum industry has for many years sought additional chemicals, which when added to a water fluid, will increase the efficiency of the water flooding method. A few of the chemicals which have been found useful for this purpose are surfactants, solubilizers, polymers, sacrificial agents, caustic additives and other reservoir conditioning agents.

The greater efficiency achieved by the addition of these chemicals to a water fluid is offset by the high cost of the chemicals themselves. In order for a petroleum recovery operation to be economically justifiable the value of the petroleum recovered by the process must, of course, exceed the cost of the recovery process itself. It is also known that most, if not all, of these chemicals are, to varying degrees, retained within the reservoir rock and are not to any large extent recoverable during the course of the petroleum recovery operation. To this end there is a substantial need to be able to accurately predict the amount of any such chemical that will be retained within the reservoir rocks during the course of the petroleum recovery operation. Knowledge of such an amount is crucial to the design of the chemical flood program.

Several different types of methods have been proposed for determining the chemical requirements for a chemical flooding program in which the amount of the chemical retained within the formation is determined. Such methods range in complexity from small scale laboratory bench testing of core materials to large scale multiwell pilot tests in the field. Unfortunately laboratory data are often unable to accurately predict chemical retention values under reservoir conditions due to the difficulties involved in translating information obtained from core flooding tests into information that is applicable to the immense heterogeneous reservoir rock volumes that comprise a typical petroleum reservoir. On the other hand, while a large scale multiwell pilot testing program will usually be able to provide fairly accurate chemical retention data, the costs involved in both expense and time in such programs are often prohibitive. In between these two methods fall methods involving only a single well to determine chemical retention data, bridging the gap between the laboratory and pilot floods. This type of procedure is attractive because a sufficiently large volume of reservoir is contacted to give meaningful results, and the results are usually able to be obtained within reasonable time and cost limits. One such technique is disclosed in the June 1967 issue of the *Journal of Petroleum Technology* in a paper by H. R. Froning and R. O. Leach entitled "Determination of Chemical Requirements and Applicability of Wettability Alteration Flooding." Nevertheless, although the method has appeared promising, the methodology employed to extrapolate the data obtained from these single well test methods to the reservoir as a whole has been suspect and there remains a present need for a method which will produce accurate, reliable results.

SUMMARY OF THE INVENTION

The amount of a chemical that is retained within a subterranean reservoir undergoing a chemical flooding operation is determined by:

(a) conducting a first injection-soak-production cycle in a single well with a volume of fluid comprising the chemical and a non-retained tracer material;

(b) obtaining from a produced fluids concentration profile of the tracer the reservoir volume contacted by the tracer and a dispersion parameter which describes the dispersion effects that take place for a non-retained material within the reservoir;

(c) obtaining retention parameters for the retained chemical by utilizing dispersion data from step (b) and comparing the actual produced fluids concentration profile for the retained chemical with a simulated produced fluids concentration profile for the retained chemical obtained from a chemical flood mathematical model of the reservoir;

(d) conducting at least one more injection-soak production cycle in the well utilizing a fluid of the same volume and comprising the same concentration of the retained chemical and the non-retained tracer as in step (a), and comparing the simulated produced fluid concentration profiles of the retained chemical and the non-retained tracer against the actual produced fluid concentration profiles of this step for an acceptable match, modifying as necessary the retention parameters;

(e) simulating additional cycles in the well until such time as the simulated produced fluids concentration profile for the retained chemical(s) is essentially the same as the actual produced fluid concentration profile for the tracer from step (a); and (f) determining the amount of chemical retained within the contacted reservoir volume by summing the amounts of chemical retained in step (a) and steps (d) and (e).

BRIEF DESCRIPTION OF THE DRAWINGS

FIG. 1 is a graph of the produced fluid concentration profiles for both retained chemical and a non-retained tracer in a generalized series of cyclic tests in a single well.

FIGS. 2 and 5 are graphs of the normalized produced KI and CL⁻ (the tracers) concentration histories from the field (experimental) test.

FIG. 3 is a graph of the first cycle produced surfactant (the retained chemicals) concentration history.

FIG. 4 is a graph of the second cycle produced surfactant concentration history.

FIGS. 6 and 7 are graphs of the production responses of two separate retained chemicals, and tracer.

FIGS. 8 and 9 are graphs of the concentration and retention distributions as a function of distance from the injection well for two separate retained chemicals and tracer.

DESCRIPTION OF THE PREFERRED EMBODIMENTS

Reliable data concerning chemical retention in a reservoir is vital for designing the chemical flood within a reservoir. Such data are usually obtained from laboratory experiments involving chemical injection into core materials obtained from the reservoir. It is, however, difficult to extrapolate the data obtained from laboratory core floods to the reservoir as a whole because of the inability of the core flood to accurately simulate the complex fluid flow and chemical retention mechanisms that take place within the comparatively huge volume of a typical heterogeneous subterranean reservoir. Reliable data can be obtained from a multiwell pilot program wherein the actual chemicals are injected through and produced from a plurality of wells which penetrate a portion of the reservoir. Such a procedure is, however, very costly and quite time consuming and is almost certainly too expensive, typically on the order of several million dollars, to ever be able to be put to widespread use as a test for chemical retention. An alternative method does exist however for determining chemical retention data within a reservoir. This alternative involves a short duration, low cost field test using only a single well. The procedure involves injecting a relatively small quantity of an aqueous chemical solution comprising both a "target" chemical and a non-retained tracer through the well into the subterranean reservoir. The well is then shut-in for a few days to satisfy chemical consumption in the effected reservoir volume and is finally put on production while the produced fluids are monitored for the concentration of both the chemical and the tracer. Chemical retention values can then be determined by material balances on the injected and produced chemical and tracer. Our invention concerns novel refinements on this basic technique which markedly improve the accuracy and reliability of the chemical retention values which can be obtained by the method.

This cycle chemical retention test employs a plurality of injection-soak-production cycles in which the same quantity of fluid is injected in each cycle and comprises a non-retained tracer and the chemical(s) for which reservoir retention data are desired. Since the same quantity of fluid is injected in each cycle and the tracer material is not retained and assuming that no injected fluid is lost due to drift effects within the reservoir and that the fluid saturation that is within the reservoir remain virtually unchanged, the reservoir volume contacted by the tracer will be essentially the same in each cycle. However, the reservoir volume contacted by an injected chemical(s) would be less than the reservoir volume contacted by the non-retained tracer due to chemical retention. The reservoir volume contacted by the chemical would eventually equalize with the tracer contacted volume after a number of repetitions of the injection-soak-production cycle as the chemical retention requirements within the effected reservoir volume became satisfied. This is illustrated in FIG. 1. The point at which the chemical retention requirements are satisfied can be determined by comparing the concentration profiles for the produced tracer and chemical. This point is reached when the concentration profile of the produced chemical becomes essentially identical to that of the concentration profile of the produced tracer. A unit value for the chemical retention within the reservoir can then be obtained by summing the amount of chemical retained within the reservoir during each cycle and then dividing by the affected reservoir volume.

In many cases however, the number of cycles necessary to reach this end point can be large enough to be considered to be impracticable from an economic viewpoint. In those cases where the number of cycles must be limited, the actual pore volume of the reservoir that acts upon and retains the chemical is not equal to the injected volume of fluid in the cycle. A technique must be found which can determine the reservoir volume that does retain the chemical. Our method utilizes a computer-implemented mathematical model which simulates the fluid flow and chemical interactions that take place within a reservoir during a chemical flood. Initially, the tracer concentration profile obtained in the produced fluids at the end of the first cycle is utilized to obtain a dispersion parameter which describes the dispersion effects that take place for the non-retained tracer material. The retained chemical concentration profile from the produced fluids at the end of the first cycle is then history-matched to obtain the retention characteristics for the first cycle. This involves determination of dispersion and retention constants which are then utilized within the mathematical model to simulate a number of repetitions of the injection-soak-production cycle until the chemical retention endpoint is reached. Unit chemical retention values for the reservoir are then determined as indicated above by summing the amounts of chemical retained during each cycle and dividing this total by the affected reservoir volume. It is preferred that a second actual injection-soak-production cycle be performed in the field to provide data useful in checking the accuracy of the derived dispersion and retention parameters used in the corresponding simulated second injection-soak-production cycle and thereby determining the accuracy of the simulated results.

The mathematical model used in our invention is based on a versatile enhanced oil recovery program designed for the simulation of either linear or pattern water floods, surfactant floods or combination floods in either a single layer or a stratified reservoir. It is based on stream tube concepts and is designed to handle injection of solutions containing up to four chemicals. The model is designed to handle: (1) chemical transport mechanisms, accounting for dispersion, retention and partitioning effects; (2) incompressible flow of both water and oil phases within either the high tension (immiscible) or low tension (miscible) fluid flow regimes depending upon the chemical environment; and (3) non-Newtonian flow of an injected polymer solution and associated permeability reduction effects due to polymer retention within the reservoir matrices. The model as utilized herein simulates a single well cyclic retention test by considering injection into a five spot pattern consisting of one centrally located injection well and the corresponding surrounding production wells. The stream tube model represents essentially a radial flow in a cyclic test since the volume of the injected fluid is relatively small. The injection and production from the same well is simulated by switching the centrally located well in the five spot pattern from initial injection mode to a production mode after a suitable shutin (soak) period.

The basic fluid flow and chemical transport equations used in the model are:
Linear Two-Phase Incompressible Flow Equations:

$$-q_t \frac{\partial f_w}{\partial x} = \phi A \frac{\partial S_w}{\partial t}$$

where $$f_w = \frac{q_w}{q_t} = \frac{q_w}{q_w + q_o} = \frac{\frac{k_{rw}}{\mu_w}}{\frac{k_{rw}}{\mu_w} + \frac{k_{ro}}{\mu_o}}$$

$$f_w + f_o = 1.0$$

$$S_w + S_o = 1.0$$

where $f_w$=fractional water flow, $cm^3/cm^3$; $f_o$=fractional oil flow, $cm^3/cm^3$; x=distance, cm; A=cross-sectional area, $cm^2$; $S_w$=water saturation, $cm^3/cm^3$; $S_o$=oil saturation, $cm^3/cm^3$; t=time, sec; $q_w$=water flow rate, $cm^3/sec$; $q_o$=oil flow rate, $cm^3/sec$; $q_t$=total flow rate, $cm^3/sec$, $k_{rw}$=water relative permeability; $k_{ro}$=oil relative permeability; $\mu$=viscosity, mPa-s (cP).

Linear Dispersion-Retention-Partitioning Equations:

$$\frac{\partial}{\partial x}\left(D\frac{\partial C_w}{\partial x}\right) - \frac{q_t}{A}\frac{\partial}{\partial x}(f_w C_w + f_o C_o) =$$

$$\phi \frac{\partial}{\partial t}(S_w C_w + S_o C_o) + (1 - \phi)\rho_r \frac{\partial C_{rm}}{\partial t}$$

$$\rho_r \frac{\partial C_{rm}}{\partial t} = K_1(K_3 - C_{rm})C_w - K_2 C_{rm}$$

where $C_w$=concentration in the water phase, $mg/cm^3$; $C_o$=concentration in the oil phase, $mg/cm^3$; $\phi$=porosity, $cm^3/cm^3$; $\rho_r$=rock density, $gm/cm^3$; $C_{rm}$=chemical retention, mg/g of rock; $K_1$=kinetic adsorption rate constant, g/mg-sec; $K_3$=maximum equilibrium retention, mg/g; $K_2$=kinetic desorption rate constant, g/ml-sec.

The oil phase chemical concentration and dispersion coefficients are given as follows:

$$C_o = K C_w$$

$$D = \lambda \frac{(q_t)}{A\phi} = \lambda v$$

where D=dispersion coefficient, $cm^2/sec$; K=partition coefficient, dimensionless; $\lambda$=dispersion parameter, cm; v=interstitial velocity, cm/sec.

The high, low or intermediate tension flow behavior is influenced by the aqueous phase chemical and salt concentrations. The flow behavior is simulated by using appropriate relative permeability data. High tension oil-water relative permeability curves are the same as used for conventional water flood calculations. A provision is made to account for residual resistance due to polymer retention on the rock. The low tension relative permeabilities are similar to those used for miscible displacements. Modified Corey equations are used to determine relative permeability as follows:

$$k_{rw} = \frac{S_w - S_{wir}}{1 - S_{wir}}^{n_w}$$

$$k_{ro} = \frac{S_o - S_{or}}{1 - S_{wir} - S_{or}}^{n_o}$$

where $S_{or}$=residual oil saturation, $cm^3/cm^3$; $S_{wir}$=irreducible water saturation, $cm^3/cm^3$, $n_o$=oil relative permeability exponent; $n_w$=water relative permeability exponent.

The exponents $n_w$ and $n_o$ approach unity, and $S_{or}$ approaches zero in the case of very low tension. The above relationships may be used for high or intermediate tension for which the exponents are greater than unity and $S_{or} > 0$.

The model allows polymer viscosity to be a function of its aqueous phase concentration and shear rate. The apparent polymer viscosity is related to shear rate at a given concentration, as reported by G. J. Hirasaki and G. A. Pope in the August 1974 issue of the *Society of Petroleum Engineering Journal* at page 237 entitled "Analysis of Factors Influencing Mobility and Adsorption in the Flow of Polymer Solution Through Porous Media". The finite difference shceme presented by J. T. Patton, K. H. Coates and J. T. Colagrove in the March 1971 issue of *The Society of Petroleum Engineering Journal* at pages 72–84 entitled "Prediction of Polymer Flood Performance" is used to solve for fluid saturations. The system of chemical transport equations is solved for a chemical concentrations in the aqueous, oil, and solid phases using the finite difference technique developed by A. Satter, Y. M. Shum, W. T. Adams and L. A. Davis in SPE Paper 6847 presented at the 52nd Fall Meeting of the SPE of AIME in Denver, Colo., Oct. 9–12, 1977 entitled "Chemical Transport in Porous Media". The injection rate, which is allowed to vary during the life of a flood, is allocated among the stream tubes of various layers according to the fluid mobilities in the tubes based again on the Patton reference.

The computer program starts by calculating the cell and tube geometrical data based upon input streamline information and initializes the fluid saturations and chemical concentrations in the cells of the tubes of the various layers; then, starting at the initial time, computations are carried out by time steps. The sequence of calculations carried out includes mobilities in the cells, injection rate into a cell when pressure differential between the injector and producer is fixed or vice versa, followed by flowrates through the tubes. Then, considering one tube at a time, fluid saturations and fractional flows and concentrations of each chemical in the aqueous, oil or solid phases in the cells are computed. The output consists of oil, water and chemical production, fluid saturations, and chemical distributions in the reservoir at specified time intervals.

The operability of the mathematical simulator and the method of our invention was verified in a series of laboratory experiments. The results of these experiments form the basis for our related application Ser. No. 61964 filed of even date. The method of our invention was also applied to an actual field test, the results of which are reported in the example below.

EXAMPLE 1

A field trial of the method of our invention was designed and carried out in the Manvel field in Brazoria County, Tex. The particular oil well utilized had been completed at a depth interval of from 1,709 m to 1,717 m in the A-1 Oligocene sand member of the Manvel reservoir. The well was gas lifting 95 to 110 m³ per day of fluid with a 3-4% oil cut, the oil gravity, formation volume factor and viscosity are 28.5° API, 1.25 m³/m³, and 1.5 mPa-s (cP) at formation temperature of 74° C. (165° F.), respectively. The reservoir properties were estimated to be: porosity, 0.31 m³/m³ permeability, 471 md; oil saturation, 0.34 m³/m³; and salinity (total dissolved solids), 107,000 g/m³ (PPM).

The well was subjected to three cycles, each composed of three phases: injection of enhanced oil recovery chemicals and tracers, soak, and production. The details are presented in Table 1 below:

TABLE 1

BASIC CYCLIC TEST DATA

| | CYCLE | | |
|---|---|---|---|
| | No. 1 | No. 2 | No. 3 |
| Injection Date | 7-12-77 | 7-29-77 | 8-18-77 |
| Injection Time, days | 2 | 2 | 2 |
| Injected Volume, m³ | 159 | 159 | 157 |
| Injection Concentration, g/m³ | | | |
| TRS 18/40[1] | 11,252 | 12,349 | — |
| Adduct N-60 CS[2] | 6,924 | 6,213 | — |
| KI (Tracer) | 362.5 | 341.8 | 382.3 |
| Soak Time, days | 2 | 2 | 2 |
| Production Time, days | 7.4 | 10.6 | 5.9 |
| Produced Volume, m³ | 590 | 843 | 469 |

[1]TRS 18/40 is a petroleum sulfonate surfactant blend marketed by the Witco Chemical Company.
[2]Adduct N-60 CS is an anionic surfactant of the following formula:
$CH_3(CH_2)_8$—$(C_2H_4O)_{6.0}$—$C_2H_4$—$(SO_3)^-$ Prior to the initiation of the test, water alone was injected to ascertain a stable injection rate. The production rate was kept lower than the pre-test well production rate so as to prevent possible sanding problems from the unconsolidated formation and to minimize possible water influx drift rate during the tests. The injection/production rates, and the total volume of fluid injected were maintained virtually the same in each cycle. Factors such as formation thickness, porosity, permeability variation, reservoir fluid drift rate, residual oil saturation due to surfactant displacement, chemical dispersion, adsorption-desorption characteristics and the desired extent of penetration of the chemical solution away from the wellbore were considered in determining the injection/production volumes and soak time. The chemical solution was brought to the well site through a temporary injection line from an injection plant via a production well tank battery. This arrangement enabled a section of the line from the tank battery to the test well to be used in the reverse mode during the production cycle when the test well production was gauged at the tank battery. Care was taken to purge clean all lines with water prior to their use for carrying the chemical solution. The tracer solutions were prepared at the well site and added to the injection stream. Difficulty was encountered in maintaining constant tracer concentration for the first and second cycle injections since the solutions were prepared by batches. Methanol tracer was also used in the first and second cycles. However, its injection concentrations turned out to be unreliable due to methanol losses by evaporation and were not used in the third cycle. The potassium iodide (KI) injection data for the third cycle were the most reliable since the tracer solution was prepared in a single batch.

Samples of produced fluids were collected at the wellhead in quart bottles, and the cumulative water and oil production volume was recorded at the time of each sampling. The frequency of sampling varied from hourly during the first two days of cyclic production to an interval of four hours towards the end of the production phase. An adequate number of samples was analyzed for surfactant, tracer and chloride contents in order to insure accurate response definition.

The collected data was then analyzed. The amounts of injected KI, TRS 18/40 and N-60 CS produced from the well were determined by integrating the product of the flow rate and concentration of each with respect to time. Injection and production data obtained from the test are presented in Table 2.

TABLE 2

INJECTION AND PRODUCTION DATA

| | Components | | | | |
|---|---|---|---|---|---|
| | KI | Cl | TRS 18/40 | N-60 CS | TRS 18/40 & N-60 CS |
| Injected, kg. | | | | | |
| 1st Cycle | 57.6 | | 1,797.5 | 1,106.1 | 2,903.6 |
| 2nd Cycle | 54.3 | | 1,977.2 | 994.8 | 2,972.0 |
| 3rd Cycle | 60.0 | 1,894.5 | | | |
| Produced, kg. | | | | | |
| 1st Cycle | 60.9 | | 640.2 | 358.6 | 998.8 |
| 2nd Cycle | 50.2 | | 1,105.9 | 662.7 | 1,768.6 |
| 3rd Cycle | 59.9 | | | | 102.0 |
| Post-Test | | | | | 1,176.2 |
| Cum. Produced, Frac. Cum. Inj. | | | | | |
| 1st Cycle | 1.057 | | 0.356 | 0.324 | 0.344 |
| 2nd Cycle | 0.993 | | 0.463 | 0.486 | 0.471 |
| 3rd Cycle | 0.995 | | | | 0.488 |
| Post Test | | | | | 0.689 |

A considerable amount of surfactant was produced with oil during the several months of production of the well following the cyclic test. Production phases during the test yielded emulsions accompanied by a reduction in the oil cut. It persisted during the early post-test production period. However, the well returned eventually to its normal oil cut.

Material balance calculations on the non-retained tracer (KI) indicate some discrepancy between the amounts produced and injected for both the first and second cycles. This can be attributed to the fact that the injected tracer solutions for these two cycles were prepared in several different batches wiich resulted in the concentration variation. In contrast, the tracer solution for the third cycle was prepared uniformly in a single batch and the material balance shows that the injected tracer was entirely recovered. To account for this discrepancy in the first and second cycles the injected concentration was adjusted upward in the case of the first cycle and downward in the case of the second cycle so as to balance the amounts injected and produced. These adjusted injection concentrations were then used to normalize production concentrations. FIG. 2 presents the normalized produced KI concentration histories for the three cycles. Also shown in this figure is the normalized produced Cl⁻ concentration history for the third cycle. The results show that the tracer and chloride production responses are basically the same. Therefore, the fluid flow behavior in the affected region around the well did not materially alter from the first to the subsequent cycles. The results also indicate that no loss of the injected fluid occurred due to drift, thief zones or any other phenomenon. FIGS. 3 and 4 show that the TRS 18/40 and N-60CS produced surfactant concentration ratios in both cycles varied from their constant injection concentration ratios suggesting possible chromatographic separation or differential retention of the components. However, errors introduced in analyzing the components, particularly at the lower concentration range, would necessarily affect their concentration ratio. Therefore, interpretation of the produced concentration ratio behavior is at best qualitative.

Since the KI injection data for the third cycle were the most reliable, the third cycle KI produced concentration was history-matched first by model simulation. The test well was considered for modeling purposes centrally located in a 0.1 hectare 5-spot pattern with a 2.44 meters thick reservoir pay zone. Then the first cycle KI production response was history-matched to yield the value of the dispersion parameter, (shown in FIG. 5), and the first cycle TRS and N-60 CS surfactant produced concentrations were also history-matched in order to obtain their retention characteristics. Finally, using the derived dispersion and retention characteristics (shown in Table 3 below) the second cycle produced surfactant responses were simulated.

TABLE 3

| RETENTION CHARACTERISTICS | | |
|---|---|---|
| | TRS 18/40 | N-60 CS |
| Maximum equilibrium retention, mg/g | 5.0 | 3.5 |
| Adsorption rate constant, g/mg-day | 5.25 | 8.53 |
| Desorption rate constant, g/mg-day | 0.525 | 0.525 |

The simulation results were compared with the actual produced fluids concentrations. FIG. 6 illustrates the comparisons between the actual and simulated TRS and KI produced fluids responses with the simulated response curves being represented by the solid lines compared with the actual field data represented by the discreet points in the figure. FIG. 7 illustrates the comparison for N-60 CS and KI in the same manner. These figures show that the first cycle history match results for both surfactant components are excellent and the simulated second cycle N-60CS production response compared well with the field data as well, while the TRS produced fluids comparison suffered. The sensitivities of retention characteristics and the possibility of reservoir pay zone thickness alteration during the test were then investigated. Yet, these analyses did not resolve into a better match for the case of the TRS response in the second cycle.

The mathematical model was then used to simulate the aqueous phase concentrations of the various chemicals and the surfactant retention distributions within the reservoir. The reservoir volumes retaining the surfactant components in both cycles were determined from their retention distributions shown in attached FIGS. 8 and 9. In the lower graphs in FIGS. 8 and 9, the solid curves represent the amount of surfactant retained within the reservoir at the end of the soak stage and at the end of the production stage of the first cycle while the dashed curves represent the corresponding information for the second cycle. Unit chemical retentions were then calculated using the affected reservoir volumes and the actual injection and production data. Both the maximum unit retention value, a measure of the most amount a reservoir formation will retain a chemical, and the residual retention value, a measure of a permanent loss of a chemical to the formation, are presented in Table 4. It should be noted that the cyclic residual data as shown should not be taken as the absolute minimum because all of the post-test surfactant production was not fully accounted for because monitoring of the produced fluids was discontinued.

TABLE 4

| CHEMICAL RETENTION RESULTS | | | |
|---|---|---|---|
| | TRS 18/40 | N-60 CS | TRS 18/40 & N-60 CS |
| Cumulative Retained, kg | | | |
| 1st Cycle | 1,157.3 | 747.5 | 1,904.8 |
| 2nd Cycle | 2,028.6 | 1,079.6 | 3,108.2 |
| 3rd Cycle | | | 3,006.2 |
| Post Test | | | 1,830.0 |
| Penetration Radius, m | | | |
| 1st Cycle | 5.6 | 5.4 | |
| 2nd Cycle | 6.7 | 6.3 | |
| Contacted Volume, m³ | | | |
| 1st Cycle | 178.8 | 161.5 | 170.2* |
| 2nd Cycle | 279.1 | 240.5 | 259.8* |
| Maximum Retention, mg/cc (mg/g rock) | 8.9 (5.0) | 6.3 (3.5) | 15.2 (8.5) |
| Residual Retention, mg/cc (mg/g rock) | | | |
| 1st Cycle | 6.5 (3.6) | 4.6 (2.6) | 11.2 (6.3) |
| 2nd Cycle | 7.3 (4.1) | 4.5 (2.5) | 12.0 (6.7) |
| 3rd Cycle | | | 11.6 (6.5) |
| Post Test | | | 7.0 (3.9) |

*TRS 18/40 and N-60 CS average

In the preceding preferred embodiment and accompanying example, the injection-soak-production of a nonretained tracer material was utilized to construct a produced fluids concentration history curve depicting the response of a chemical that would not be retained by the reservoir surfaces in which it came into contact during the injection-soak-production cycle. As explained above the information obtained from such a curve yields information vital to the practice of the method of our invention namely the pore volume of reservoir contacted and the retention parameter of the retained chemical. As discussed above, this produced fluid concentration curve for a non-retained tracer material will be identical in form to the produced fluid concentration curve of a chemical that is retained by the reservoir when a sufficient number of injection-soak-production cycles involving the retained chemical have been performed so that the retention demands of the reservoir for the particular volume of injected chemical have been totally satisfied. It is therefore also possible to forego the injection of a nonadsorbing tracer material in order to obtain the necessary curve and the information contained therein if the curve can be reliably obtained by other means. One such means would be to repeat the injection-soak-production cycle for the retained or target chemical a number of times until a point is reached where the last two produced chemical concentration curves are virtually the same, thus signaling that the point of maximum retention of the chemical by the reservoir has been essentially reached. In another preferred embodiment the injection-soak-production cycle for the target chemical is repeated only a number of times sufficient to be able to accurately predict the final shape of the curve by conventional techniques.

The invention and the best mode contemplated for applying that invention have been described. It is to be understood that the foregoing is presented for the purpose of illustration and that other means and techniques can be employed without departing from the true scope of the invention as defined in the following claims.

We claim:

1. A method for determining the amount of a chemical that is retained within a subterranean reservoir undergoing a chemical flooding operation comprising:
    (a) conducting a first injection-soak-production cycle in a single well which penetrates and communicates with a portion of the reservoir with a volume of a fluid which comprises the retained chemical and a non-retained tracer material;
    (b) obtaining from a produced fluids concentration profile of the tracer the reservoir volume contacted and a dispersion parameter describing the dispersion effects for a non-retained material within the reservoir;
    (c) obtaining retention parameters for the retained chemical by history-matching the actual produced fluids concentration profile of the retained chemical with a simulated produced fluids concentration profile of the retained chemical for this cycle obtained from a chemical flood mathematical model of the reservoir;
    (d) simulating within the chemical flood mathematical model at least one more injection-soak-production cycle in the well utilizing a fluid of the same volume and comprising the same concentration of the retained chemical as in step (a) until such time as the simulated produced fluid concentration profile of the chemical is essentially the same as the actual produced fluid concentration profile of tracer from step (a);
    (e) determining the amount of chemical retained within the contacted reservoir volume for the cyclic test by summing the amount of the chemical retained in step (a) and the amounts of the chemical retained in the simulated cycles of step (d);
    (f) determining the amount of the chemical that is retained per unit volume by those portions of the reservoir undergoing the cyclic test by dividing the summed amount of chemical retained in step (e) by the reservoir volume contacted in the cyclic test from step (a); and
    (g) determining the total amount of chemical retained within those portions of the reservoir as a whole that undergo the chemical flood from the information in step (f).

2. The method of claim 1 comprising an additional step wherein produced fluids concentration profiles are obtained from a second actual injection-soak-production cycle conducted in the well which are compared with the corresponding simulated produced fluids concentration profiles for the purpose of verifying the accuracy of the simulations.

3. The method of claim 2 comprising an additional step wherein, if the actual second cycle produced fluids concentration profiles differ from the corresponding simulated profiles by more than an acceptable level, the retention and dispersion parameters from steps (b) and (c) of claim 1 are adjusted in order to bring the differences between the actual second cycle profiles and the corresponding simulated profile to within acceptable levels.

4. The method of claim 1 wherein the retained chemical comprises a combination of at least two different chemical compounds.

5. In a petroleum recovery method wherein chemical is injected into an underground petroleum reservoir, the chemical being of a type which will be retained to some extent within the reservoir, wherein the chemical is injected in an amount in excess of that which would be retained within the reservoir wherein the retained amount is determined by a method comprising:
    (a) conducting a first injection-soak-production cycle in a single well which penetrated and communicates with a portion of the reservoir with a volume of a fluid which comprises the retained chemical and a non-retained tracer material;
    (b) obtaining from a produced fluids concentration profile of the tracer the reservoir volume contacted and a dispersion parameter describing the dispersion effects for a non-retained material within the reservoir;
    (c) obtaining retention parameters for the retained chemical by history-matching the actual produced fluids concentration profile of the retained chemical with a simulated produced fluids concentration profile of the retained chemical for this cycle obtained from a chemical flood mathematical model of the reservoir;
    (d) simulating within the chemical flood mathematical model at least one more injection-soak-production cycle in the well utilizing a fluid of the same volume and comprising the same concentration of the retained chemical as in step (a) until such time as the simulated produced fluid concentration profile of the chemical is essentially the same as the actual produced fluid concentration profile of tracer from step (a);
    (e) determining the amount of chemical retained within the contacted reservoir volume for the cyclic test by summing the amount of the chemical retained in step (a) and the amounts of the chemical retained in the simulated cycles of step (d);
    (f) determining the amount of the chemical that is retained per unit volume by those portions of the reservoir undergoing the cyclic test by dividing the summed amount of chemical retained in step (e) by the reservoir volume contacted in the cyclic test from step (a); and
    (g) determining the total amount of chemical retained within those portions of the reservoir as a whole that undergo the chemical flood from the information in step (f).

6. The method of claim 5 comprising an additional step wherein produced fluids concentration profiles are obtained from a second actual injection-soak-production cycle conducted in the well which are compared with the corresponding simulated produced fluids concentration profiles for the purpose of verifying the accuracy of the simulations.

7. The method of claim 6 comprising an additional step wherein, if the actual second cycle produced fluids concentration profiles differ from the corresponding simulated profiles by more than an acceptable level, the retention and dispersion parameters from steps (b) and (c) of claim 1 are adjusted in order to bring the differences between the actual second cycle profiles and the corresponding simulated profile to within acceptable levels.

8. The method of claim 5 wherein the retained chemical comprises a combination of at least two different chemical compounds.

* * * * *